United States Patent [19]

Hara et al.

[11] Patent Number: 4,988,194
[45] Date of Patent: Jan. 29, 1991

[54] OPTICAL STORAGE INSPECTION UNIT CALIBRATION DISK

[75] Inventors: Shigeji Hara; Takashi Yoshizawa, both of Musashino; Kanae Kinoshita, Yokohama; Masahiko Sakamoto, Kyoto; Mitsuhiro Terada, Kyoto; Youji Suzuki, Kyoto, all of Japan

[73] Assignees: Kyocera Corporation, Kyoto; Nippon Telegraph and Telephone Corporation, Tokyo; Shindenshikogyo Corporation, Kanagawa, all of Japan

[21] Appl. No.: 210,243

[22] Filed: Jun. 23, 1988

[30] Foreign Application Priority Data

Jul. 7, 1987 [JP] Japan .............................. 62-170272

[51] Int. Cl.$^5$ .............................................. G01J 1/02
[52] U.S. Cl. .................................................. 356/243
[58] Field of Search .................. 356/243, 237; 369/44, 369/46, 47, 51

[56] References Cited

U.S. PATENT DOCUMENTS 4,571,714  2/1986  Mathews et al. ..................... 369/44

Primary Examiner—Vincent P. McGraw
Assistant Examiner—S. A. Turner
Attorney, Agent, or Firm—Spensley Horn Jubas & Lubitz

[57] ABSTRACT

A calibration disk used for an optical disk inspection unit to correct the measurement values of the mechanical characteristics, such as plane deflection and eccentricity of optical disks, and comprising at least one of three correction sections: an axial displacement correction section, a radial displacement correction section, and a focus error output voltage correction section which are formed on one or both sides of the calibration disk, concentric to the center of rotation of the disk so that measurement values, such as the surface deflection, can be corrected automatically and accurately by simply setting the calibration disk on an inspection unit.

7 Claims, 6 Drawing Sheets

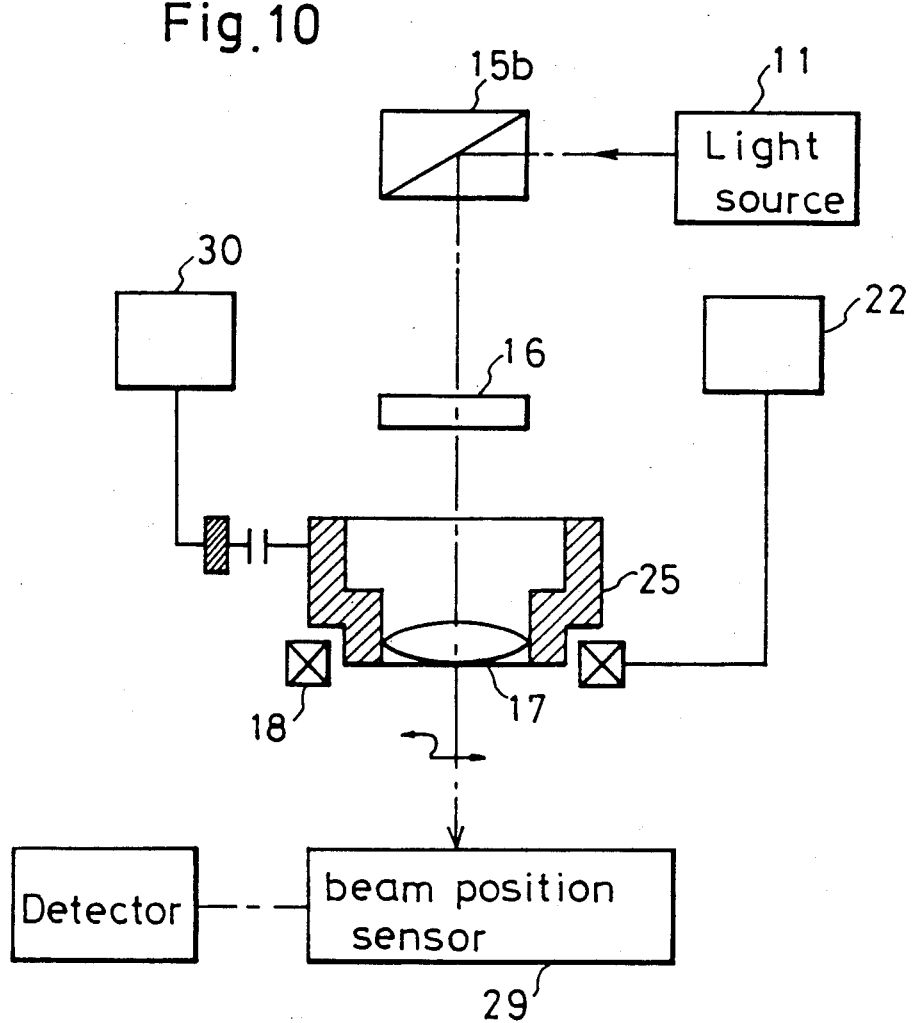

OPTICAL STORAGE INSPECTION UNIT CALIBRATION DISK

BACKGROUND OF THE INVENTION

1. Field of the Invention

The present invention relates to a calibration disk used for an optical disk inspection unit to correct the measurement values of the mechanical characteristics, such as plane deflection, eccentricity, warp angle and roundness, of optical disks including write-once disks, magneto-optical disks, and compact disks (CD).

2. Prior Art

The control accuracy of the focusing and tracking actuators of optical recording/reproducing units, such as disk players and disk recorders, is greatly dependent on the plane deflection, eccentricity and other mechanical characteristics of an optical disk. It is thus necessary to inspect that such mechanical characteristics conform to the specified standard during the production of the optical disks. By this inspection, interchangeability of the optical disks can be guaranteed.

FIG. 8 is a general block diagram illustrating an example of an optical disk inspection unit used to measure the mechanical characteristics of the optical disks described above.

Numeral 11 designates a light source (HeNe laser). Numerals 12a to 12d designate mirrors. Numeral 13 designates a half mirror. Numerals 14a and 14b designate fixed lenses. Numerals 15a and 15b designate beam splitters. Numeral 16 designates a λ/4 plate. Numeral 17 designates an object lens. Numeral 18 designates the actuator of the object lens 17. Numeral 19 designates a plane deflection measurement mirror. The object lens 17 is integrated with the plane deflection measurement mirror 19.

Numeral 21 designates a photodetector. Numeral 22 designates a focus-control circuit. The output terminal of the focus control circuit 22 is connected to the actuator 18. Numeral 23 designates an optical position sensor. A circuit including this optical position sensor 23 forms an axial displacement detection circuit. Numeral 24 designates an optical disk to be tested.

The functions of the optical disk inspection unit shown in FIG. 8 are described below.

The laser beam generated from the light source 11 is divided by the half mirror 13. A part of the beam enters the optical disk 24 (supported by the disk support 28 of the optical disk inspection unit) to be tested via the mirror 12b, fixed lens 14a, beam splitter 15a, λ/4 plate 16, mirror 12c and object lens 17.

This incident beam is reflected by the information recording plane (not shown) of the optical disk 24 to be tested. The reflected beam passes the λ/4 plate again and the deflection wave surface of the plate turns by λ/2 due to going and returning of the beam. The beam is then reflected by the beam splitter 15a and enters the photodetector 21. The photodetector 21 outputs a voltage corresponding to a focus error. The focus-control circuit 22 uses this output voltage to drive the actuator 18 so that the object lens 17 follows the recording layer deflection of the disk. The other part of the beam divided by the half mirror 13 enters the plane deflection measurement mirror 19 via the beam splitter 15b, mirror 12d and fixed lens 14b.

Since the plane deflection measurement mirror 19 follows the recording layer deflection of the disk as described above, the recording layer deflection of the disk is detected as the change of the beam spot position on the optical position sensor 23 using the beam, which enters the optical position sensor 23 via the beam splitter 15b and is reflected by the mirror 19. This change is converted into an electrical output by an axial displacement detector including the optical position sensor 23 and is used to measure the recording layer deflection of the disk.

FIG. 9 is a general block diagram illustrating another example of an optical disk inspection unit used to measure the mechanical characteristics of optical disks. This optical disk inspection unit uses a capacitance detector 27 to detect the displacement of the object lens 17 which follows the axial dynamic deflection of the disk as the change in electrostatic capacitance between a fixed electrode plate 26 and a movable electrode plate 25 installed on the object lens 17 and thus to measure the axial deflection of the disk.

The eccentricity of the disk can be measured by detecting the radial displacement of the object lens 17 which follows the tracks of the disk using the optical or capacitive displacement detector in the same way as mentioned above (Japanese Patent Application No. 60-65784).

The mechanical characteristics of the optical disk 24 are inspected as described above. Usually the inspection unit for measuring these mechanical characteristics needs to be corrected periodically to maintain its measurement accuracy. A conventional correction method is described below.

A fine adjustment jig, which has already been corrected for the displacement, is provided to the mechanical characteristics inspection unit. In order to correct the axial displacement detector, a mirror equivalent to the disk 24 is adjusted to slightly displace in the axial direction by using the adjustment jig. At this time, the object lens 17 is driven to follow the movement of the mirror by the focusing actuator controlled using the servo system composed of the photodetector 21 and focus-control circuit 22. The axial displacement detector generates an electrical output corresponding to a given axial displacement of the mirror. The correction of the axial displacement detector is made for varying displacements as mentioned above.

To correct the radial displacement detector installed on the object lens of the optical disk mechanical characteristics inspection unit, an optical system as shown in FIG. 10 is formed so that the position of the object lens 17 can be detected by using a beam position sensor 29 which has already been corrected. When the object lens 17 is driven forcibly in the radial direction, the radial displacement of the object lens 17 can be detected by the beam position sensor 29. The output of the radial displacement detector 30 obtained at this time is compared with the displacement of the object lens 17 obtained from the output of the beam position sensor 29 to calibrate the radial displacement detector 30.

In addition, the inspection unit needs to be designed by considering the installation position of the fine adjustment jig. As a result, the structure of the inspection unit is apt to become complicated. The inspection unit should be corrected frequently to maintain high optical disk measurement accuracy. In the case of the above-mentioned conventional correction method, the positional relationship between the plane deflection measurement mirror 19 and the displacement detection members needs to be adjusted very accurately. This correction method is complicated and requires much labor. There are many causes for errors, and high correction accuracy is not obtained. Furthermore, correction efficiency is low since it is difficult to automate the correction process.

SUMMARY OF THE INVENTION

It is therefore an object of the present invention to provide a calibration disk allowing accurate and efficient correction without providing any fine adjustment jig to an optical disk inspection unit. It is another object of the present invention to improve the dimensional accuracy and durability of the calibration disk and to further increase the correction accuracy of the inspection unit.

To achieve the above objects, the calibration disk of the present invention is characterized in that the disk comprises at least one of three correction sections: an axial displacement and reflectivity correction section, formed concentric to the center of rotation, which has a center correction plane with the predetermined reflectivity at the height in level with the recording layer of an optical disk, and from around the center correction plane a plurality of correction planes with the predetermined difference in level between two adjacent planes; a radial displacement correction section having a plurality of track grooves arranged at the predetermined pitch; and a focus error output voltage correction section, formed concentric to the center of rotation at the height in level with the recording layer of the optical disk, and having a surface inclined at the predetermined angle along the radial direction of the calibration disk.

With the present invention having the above structure, the axial displacement and reflectivity correction section, the radial displacement correction section and the focus error output voltage correction section are formed concentric to the rotation center of the disk, each of which provides a displacement reference, such as the predetermined difference in level, the predetermined track pitch and the inclination surface of the predetermined angle. Therefore, it is not necessary to install any fine adjustment units for calibrating the detectors on the optical disk inspection unit.

In addition, the detecting devices of optical disk mechanical characteristics, such as axial deflection and eccentricity, can be automatically corrected by simply setting and measuring the calibration disk of the present invention on the inspection unit. Thus the inspection unit can be corrected easily, efficiently, and accurately.

Furthermore, at least the circular members comprising a plurality of correction sections are made of cermet or cemented carbide. Therefore, the circular members have stable dimensional accuracy and high hardness. The circular members are also superior in weatherability and can maintain stable reflectivity. Moreover, the circular member has less thermal expansion and is stable regardless of temperature change. With these numerous features, the calibration disk as a whole can have improved durability and correction accuracy.

BRIEF DESCRIPTION OF THE DRAWINGS

FIG. 10 is a block diagram used to explain calibration of the radial displacement detector.

DETAILED DESCRIPTION OF THE INVENTION

Figure 1:
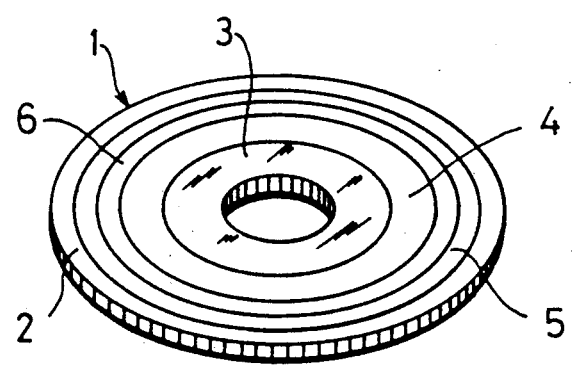
FIG. 1 is a perspective view illustrating an embodiment of the calibration disk of the present invention.

An embodiment of the present invention is described referring to FIGS. 1 to 5 (A), 5 (B) and 5 (C). The structure of the embodiment is explained first. Referring to FIG. 1, numeral 1 designates a calibration disk, numeral 2 designates a disk proper. This disk proper 2 is made of ceramic material, such as alumina, zirconia, silicon carbide or silicon nitride.

Numeral 3 designates a reference plane formed on the surface of the disk 2. The reference plane 3 corresponds to the surface of a transparent substrate of an optical disk. Numeral 4 designates the axial displacement correction section. Numeral 5 designates the radial displacement correction section. Numeral 6 designates the focus error output voltage correction section.

Figure 2:
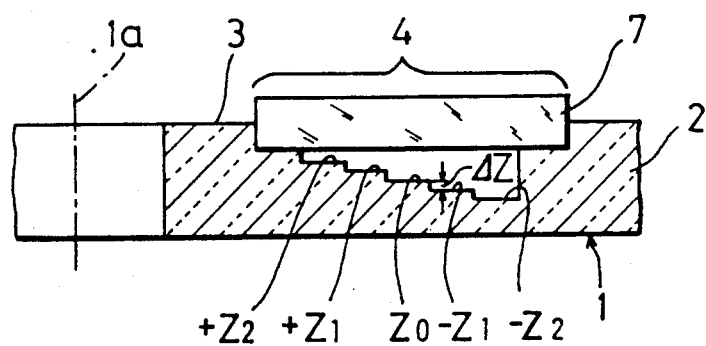
FIG. 2 is an enlarged sectional view illustrating the axial displacement correction section shown in FIG. 1.

As shown in FIG. 2, the axial displacement correction section 4 has a plurality of correction planes $+Z_2$, $+Z_1$, $Z_0$, $-Z_1$ and $-Z_2$, having the predetermined level difference $\Delta Z$ between two adjacent planes, lowering in that order just as in the case of a staircase, and concentric to the rotation center $1a$ of the calibration disk 1. $Z_0$ is a center correction plane (hereafter also referred to as plane $Z_0$). These correction planes $+Z_2$, $+Z_1$, $Z_0$, $-Z_1$ and $-Z_2$ have a good surface roughness and reflectivity so that they can be focused on by using focus-control circuit.

Figure 8:
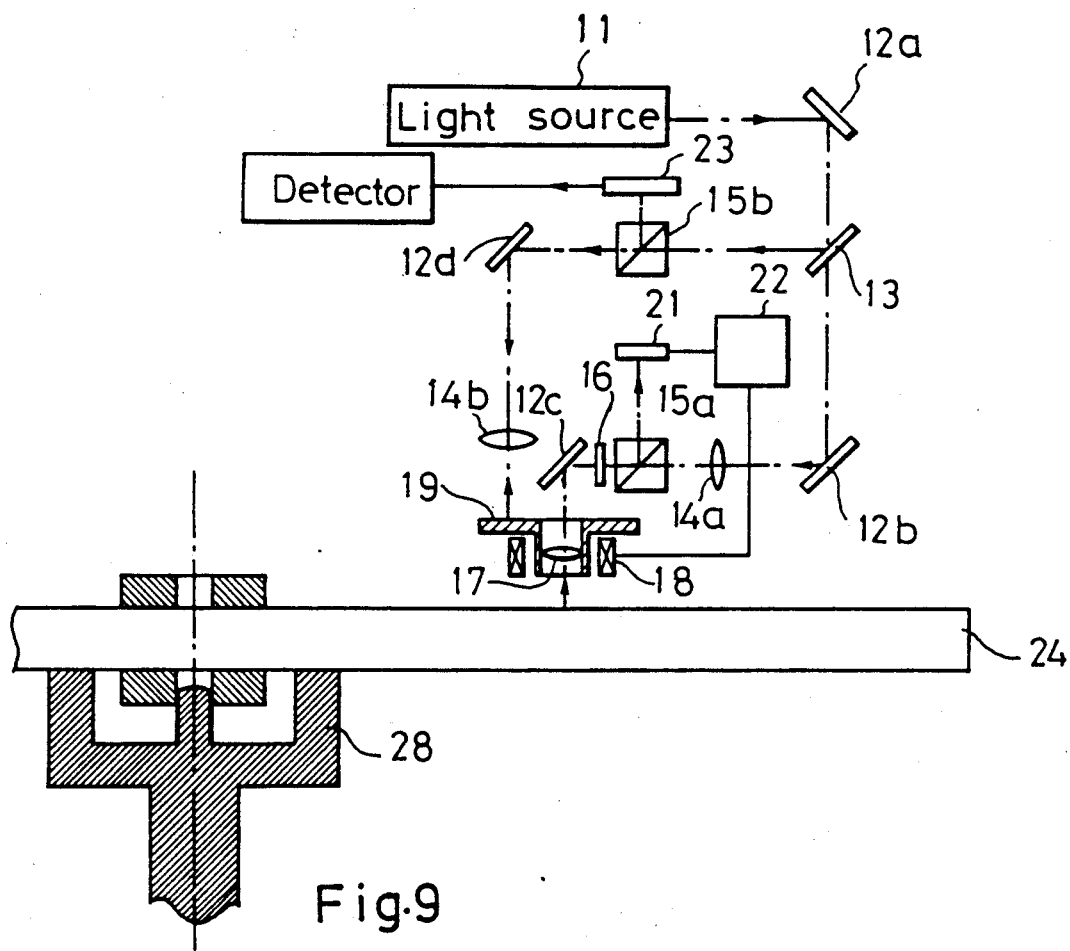
Figure 9:
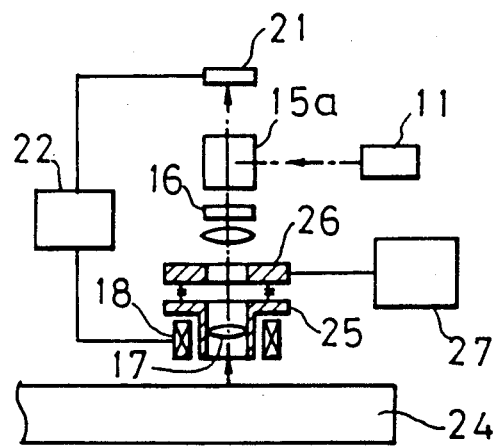

The height between the reference plane 3 and plane $Z_0$ is aligned to the distance between the disk surface and the recording layer of the optical disk, $1.2 \pm 0.01$ mm for example. When this calibration disk 1 is set on the disk support section of the optical disk inspection unit shown in FIG. 8, plane $Z_0$ is on a level with the recording layer of the optical disk.

Numeral 7 designates a cover glass provided so that the optical characteristics of the calibration disk 1 is identical to those of the real optical disk. The cover glass 7 is as thick as the transparent substrate of the optical disk.

Figure 3:
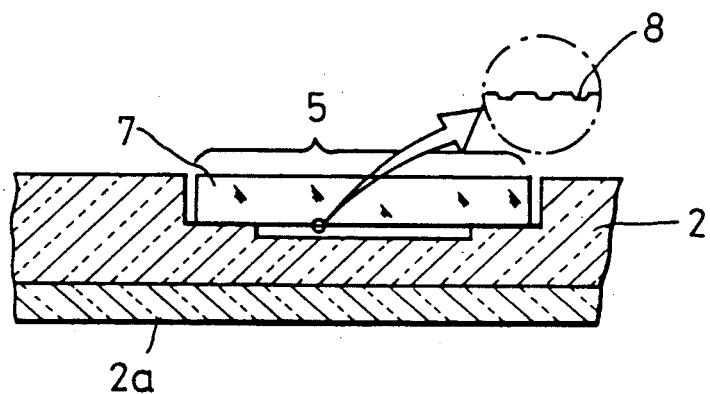
FIG. 3 is an enlarged sectional view illustrating the radial displacement correction section.

As shown in FIG. 3, the radial displacement correction section 5 has a plurality of track grooves 8 disposed at the predetermined pitch in level with the recording layer of the optical disk and concentric or spiral around the rotation center $1a$ of the calibration disk 1. A plurality of track grooves 8 can also be obtained by cutting out an approximately 10 mm wide circular section of an optical disk, which has a plurality of grooves disposed at the predetermined pitch, at 1.6 μm pitch for example, and by attaching the circular section to the predetermined position of the disk proper 2. The track grooves 8 can be provided at two or more different pitches.

Figure 4:
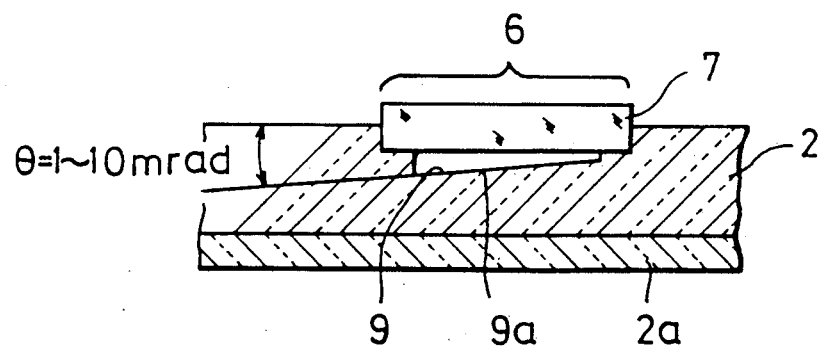
FIG. 4 is an enlarged sectional view illustrating the focus error output voltage correction section, FIGS. 5 (A), 5 (B) and 5 (C) are the output characteristic diagrams obtained from the displacement detectors of the correction sections of the embodiment shown in FIG. 1 and are used to explain correction.

As shown in FIG. 4, the focus error output voltage correction section 6 has an inclination surface 9 inclining at the predetermined angle at a circular area having a width of approximately 3 mm for example around the rotation center 1a of the calibration disk 1. The inside of the circular surface lowers 3 to 30 μm inward from the surface parallel to the reference plane 3. The inclination angle θ of the inclination surface 9 is in the range of 1 to 10 mrad. The central circular line of the inclination surface 9 is on a level with the recording layer of the optical disk and is referred to as correction reference position 9a.

The inclination surface 9 has the same surface roughness and reflectivity as those of the correction planes $+Z_2$, $+Z_1$, $Z_0$, $-Z_1$ and $-Z_2$ of the axial displacement correction section 4.

Although the inclination surface 9 inclined inward is shown in FIG. 4, the inclination surface 9 can be inclined outward. That is, the same correction function can be obtained whether the inclination surface 9 is inclined inward or outward in the radial direction of the disk proper 2.

The operation method and functions of the calibration disk having the above-mentioned structure are described below.

The calibration disk 1 is set on an inspection unit (shown in FIG. 8 for example) for inspecting the mechanical characteristics of optical disks, and the detectors of the inspection unit are corrected as described below.

When the calibration disk 1 is set on the disk support section of the mechanical characteristic inspection unit, the reference plane 3 of the calibration disk 1 is on a level with the surface of a real optical disk. The correction method of the axial displacement detector is described below referring to FIG. 5 (A). The beam spot is applied to the axial displacement correction section 4 and focus control is performed so that the focus is set on plane $Z_0$. While the beam spot position is moved to the planes $+Z_2$, $+Z_1$, $Z_0$, $-Z_1$ and $-Z_2$, the output values of the axial displacement detector are measured.

Figure 5A:
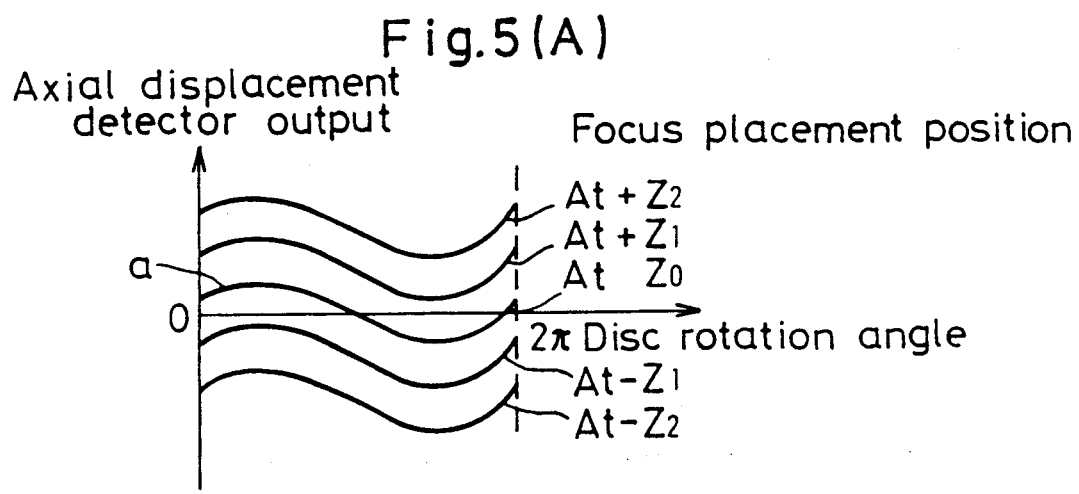
Figure 5B:
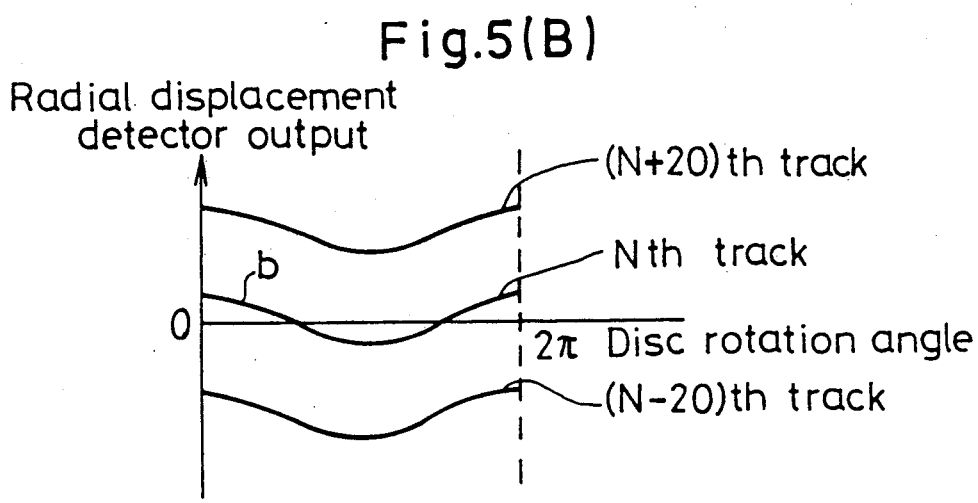
Figure 5C:
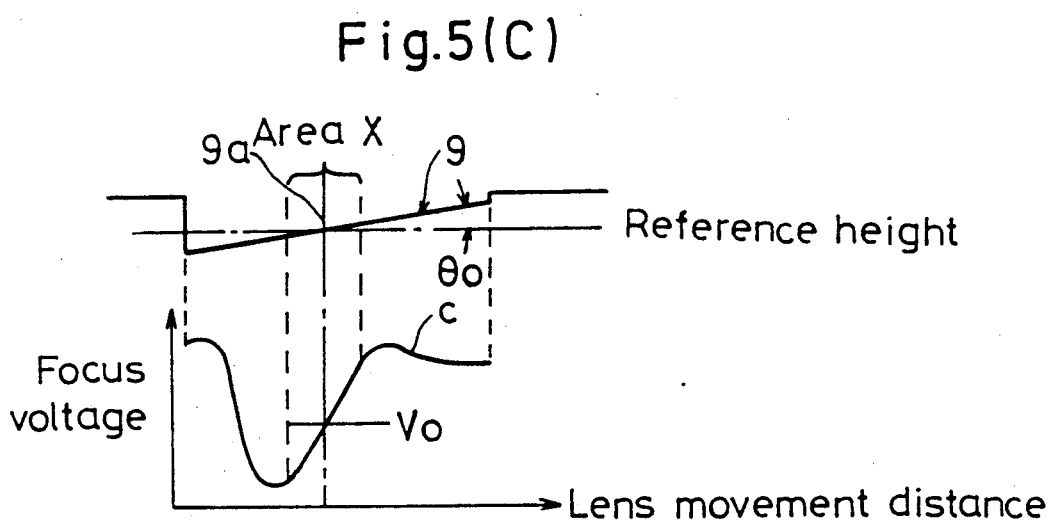

FIG. 5 (A) shows the output characteristics obtained by measuring these output values during one revolution of the calibration disk. The difference in the output direct current value corresponds to the level difference $\Delta Z$ between two adjacent correction planes ($+Z_2$, $+Z_1$, $Z_0$, $-Z_1$ and $-Z_2$). In this way, the axial displacement detector can be corrected depending on these output direct current values.

The correction method of the radial displacement detector is described below referring to FIG. 5 (B). Tracking control is performed so that the beam spot follows the Nth track groove 8 of the radial displacement correction section 5. The output of the radial displacement detector is used as radial displacement correction reference output b. Then the beam spot is moved by the predetermined distance corresponding to a constant number of tracks, 20 tracks for example, outward and inward from the Nth track, and the output values of the radial displacement detector are measured.

FIG. 5 (B) shows the output characteristics obtained by measuring these output values while the calibration disk 1 makes one rotation. The difference in these output direct current values corresponds to the lens movement distance in the radial direction, that is, the product of the known track pitch and the number of tracks.

The correction method of the focus error output voltage is described below referring to FIG. 5 (C).

First, the object lens is driven forcibly so that the beam converges to the correction reference position 9a of the focus error output voltage correction section 6. When the optical head (object lens) is moved outward and inward by approximately 1 mm for example from the reference position 9a, without performing focus control, the focus error corresponding to the inclination angle θ occurs and the output voltage corresponding to the focus error changes. This change, that is, the voltage characteristic c is shown in FIG. 5 (C). $V_0$ of the characteristic c designates the reference output voltage at the correction reference position 9a.

In the area X centered at the correction reference position 9a, the output voltage characteristic c is represented by an almost linear line. The focus error at the point (in the area X) away from the correction reference position 9a by the predetermined distance can be derived from the predetermined angle $\theta_0$. The focus error can thus correspond to the output voltage represented by the above output voltage characteristic c.

Therefore, the focus error output characteristic corresponding to a minute focus error can be corrected, provided that the focus error is within the area X. In the above embodiment, the axial displacement correction section 4 has a form of a staircase, and the beam spot is focused to each correction plane at a time. However, by providing an inclined surface (having the predetermined inclination angle) between two adjacent correction planes, the beam spot can be moved continuously over the correction planes $+Z_2$, $+Z_1$, $Z_0$, $-Z_1$ and $-Z_2$ without discontinuing focus control.

Figure 6:
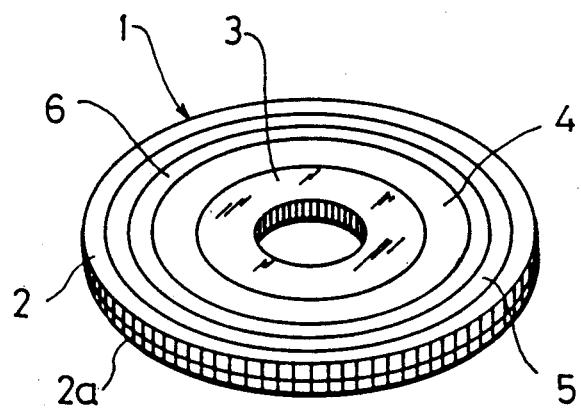
FIG. 6 is a perspective view illustrating another embodiment of the calibration disk of the present invention.

FIG. 6 shows the structure of another embodiment of the calibration disk of the present invention. A lower disk 2a, which is the same as the disk proper 2 in diameter, thinner than the disk proper 2 and made of alumina or silicon carbide, is attached to the bottom surface of the disk proper 2 made of ceramic material, such as alumina, zirconia, silicon carbide or silicon nitride.

Figure 7:
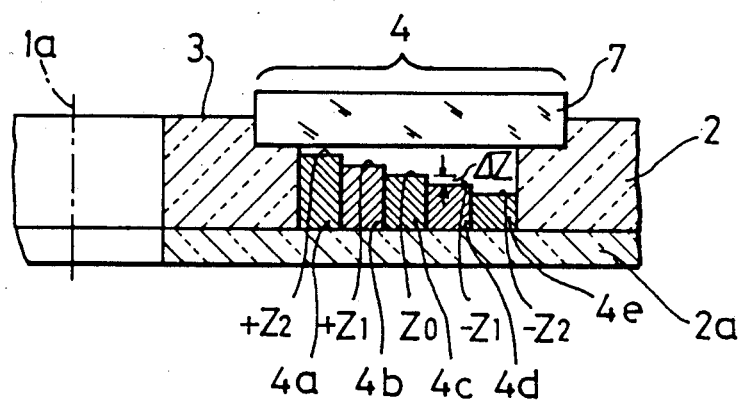
FIG. 7 is an enlarged sectional view illustrating the axial displacement correction section shown in FIG. 6, FIGS. 8 and 9 are general block diagrams of optical disk inspection units.

FIG. 7 shows the detailed structure of the axial displacement correction section 4 of the correction calibration disk shown in FIG. 6. The correction planes $+Z_2$, $+Z_1$, $Z_0$, $-Z_1$ and $-Z_2$ are formed on a plurality of circular members 4a, 4b, 4c, 4d and 4e respectively attached to the disk proper 2 and the lower disk 2a using adhesive. The circular members 4a, 4b, 4c, 4d and 4e are made of cermet or cemented carbide. The top surfaces of the circular members 4a, 4b, 4c, 4d and 4e have a surface roughness index value ($R_a$) of approximately 4 μin (0.1 μm) or less to provide correction planes having proper reflectivity.

Table 1 shows the measurement results of the characteristics of samples 1, 2 and 3. The above circular members 4a, 4b, 4c, 4d and 4e of sample 1 are made of cermet: Tic 50%–TiN 20%–$MO_2C$ 10%–WC 10%–Ni 5%–Co 5%. Those of sample 2 are made of Nbc 30%–TiC 20%–TiN 5%–WC 15%–$MO_2C$ 15%. Sample 3 is similar to sample 2 except that a half of NbC 30% used in cermet of sample 2 is replaced with TaC.

TABLE 1

| Physical property | Unit | Sample 1 | Sample 2 | Sample 3 |
|---|---|---|---|---|
| Apparent specific gravity | — | 6.0 | 7.7 | 8.1 |

TABLE 1-continued

| Physical property | Unit | Sample 1 | Sample 2 | Sample 3 |
|---|---|---|---|---|
| Vickers hardness | kg/mm$^2$ | 1650 | 1450 | 1500 |
| Rockwell hardness | kg/mm$^2$ | 92.5 | 91.5 | 92.0 |
| Bending strength | kg/mm$^2$ | 160 | 190 | 170 |
| Young's modulus | kg/cm$^2$(× 10$^6$) | 4.4 | 4.2 | 4.3 |
| Coefficient of (40 to 400° C.) linear expansion (40 to 800° C.) | 1 × °C.(× 10$^6$) | — 8.5 | 7.8 — | 7.90 8.70 |
| Thermal conductivity | Cal.cm/cm$^3$.sec. °C. | 0.03 | 0.03 | 0.02 |
| Breaking toughness | MN/m$^{\frac{3}{2}}$ | 9.0 | 9.5 | 10.5 |
| Reflectivity | % | 30–40 | 53–65 | 80–90 |

In addition, the circular members 4a to 4e made of cermet or cemented carbide material only, such as TiN, TiC or WC, also have appropriate reflectivity and can be used to form a superior calibration disk.

The optical reflectivity at the correction planes $+Z_2$, $+Z_1$, $Z_0$, $-Z_1$ and $-Z_2$ is discussed below. To carefully examine the reflectivity, the inventor of the present invention conducted various experiments and found that the best detection characteristics was obtained when the reflectivity of the top surfaces of the circular members 4a to 4e of the axial displacement correction section 4 was in the range of 17 to 93%.

Since the inclination surface 9 of the focus error output voltage correction section 6 has a very small inclination angle of several mrad, the axial displacement correction section 4 can also function as the focus error output voltage correction section 6.

Therefore, it is not necessary to provide all the correction sections 4, 5 and 6 on the calibration disk 1. Furthermore, it is not necessary to provide all the correction sections on one side of the disk proper 2, but these sections can be provided on different sides (one section on one side, and the other sections on the other side).

We claim:

1. A rotatable calibration disk used for correction of an optical disk inspection unit for optical disks having a recording layer, comprising at least one of two correction sections: an axial displacement correction section, formed concentric to a center of rotation of said calibration disk, which has a center correction plane with a predetermined reflectivity value at a height in level with the recording layer of an optical disk, and from around said center correction plane a plurality of correction planes with a predetermined difference in level between two adjacent planes; and a focus error output voltage correction section, formed concentric to said center of rotation at said height in level with said recording layer of said optical disk, and having a surface inclined at a predetermined angle along the radial direction of said calibration disk.

2. A calibration disk according to claim 1, wherein said plurality of correction planes of said axial displacement correction section of said at least one correction section have said predetermined reflectivity value.

3. A rotatable calibration disk used for correction of an optical disk inspection unit for optical disks having a recording layer, comprising three correction sections: an axial displacement correction section, formed concentric to a center of rotation of said calibration disk, which has a center correction plane with a predetermined reflectivity at a height in level with the recording layer of an optical disk, and from around said center correction plane a plurality of correction planes with a predetermined difference in level between two adjacent planes; a radial displacement correction section having a plurality of track grooves arranged at a predetermined pitch for track control; and a focus error output voltage correction section, formed concentric to said center of rotation at said height in level with said recording layer of an optical disk, and having a surface inclined at a predetermined angle along the radial direction of said calibration disk, said correction planes of said axial displacement correction section comprising circular members, wherein at least one of said circular members is made of cermet or cemented carbide.

4. A calibration disk according to claim 3, wherein said predetermined reflectivity of said circular members of said axial displacement correction section is in the range of 17 to 93%.

5. A calibration disk according to claim 3 or 4, wherein said correction planes of a plurality of said circular members of said axial displacement correction section have a surface roughness index value ($R_a$) of 4 μin (0.1 μm) or less.

6. The calibration disk of claim 1 further comprising a radial displacement correction section having a plurality of track grooves arranged at a predetermined pitch for track control.

7. A calibration disk used for calibrating an optical disk inspection unit, said calibration disk comprising at least one calibration section being formed concentric to a center of rotation of said calibration disk and comprising nonencoded surfaces of different heights.

* * * * *